United States Patent [19]

Putz

[11] Patent Number: 4,903,702

[45] Date of Patent: Feb. 27, 1990

[54] BRAIN-CONTACT FOR SENSING EPILEPTOGENIC FOCI WITH IMPROVED ACCURACY

[75] Inventor: David A. Putz, Racine, Wis.

[73] Assignee: Ad-Tech Medical Instrument Corporation, Racine, Wis.

[21] Appl. No.: 286,763

[22] Filed: Oct. 17, 1988

[51] Int. Cl.$^4$ ............................................. A61B 5/04
[52] U.S. Cl. ................................................. 128/642
[58] Field of Search ................ 128/642, 658, 784–786, 128/305 B; 604/280

[56] References Cited

U.S. PATENT DOCUMENTS

| | | | |
|---|---|---|---|
| 3,605,750 | 9/1971 | Sheridan et al. | 604/280 X |
| 4,245,645 | 1/1981 | Arseneault et al. | 128/642 |
| 4,735,208 | 4/1988 | Wyler et al. | 128/642 |
| 4,796,637 | 1/1989 | Mascuch et al. | 604/280 X |

FOREIGN PATENT DOCUMENTS

| | | | |
|---|---|---|---|
| 0236285 | 9/1987 | European Pat. Off. | 128/784 |
| 2504394 | 10/1982 | France | 128/642 |
| 0241688 | 12/1986 | German Democratic Rep. | 128/642 |

*Primary Examiner*—Lee S. Cohen
*Attorney, Agent, or Firm*—Peter N. Jansson, Ltd.

[57] ABSTRACT

An improved electrical brain-contact device for increased accuracy in determining epileptogenic foci. The intracranial device has a dielectric base member and an array of contacts mounted thereon with separate leads extending therefrom, and is characterized by radiopaque dielectric means adjacent to at least one of the contacts such that the positions of the contacts of the array may more readily be determined by x-ray. Certain preferred forms have discrete radiopaque dielectric markers in various arrangements, including sub-arrays of markers corresponding in number and positions to subsets of the contacts.

20 Claims, 2 Drawing Sheets

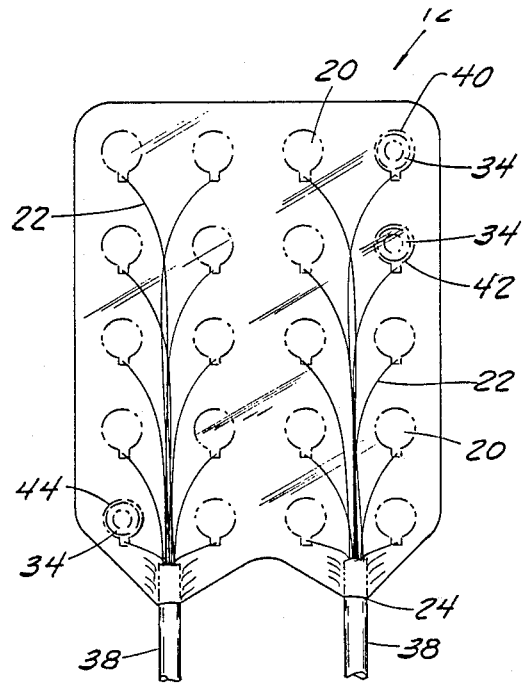
FIG. 4
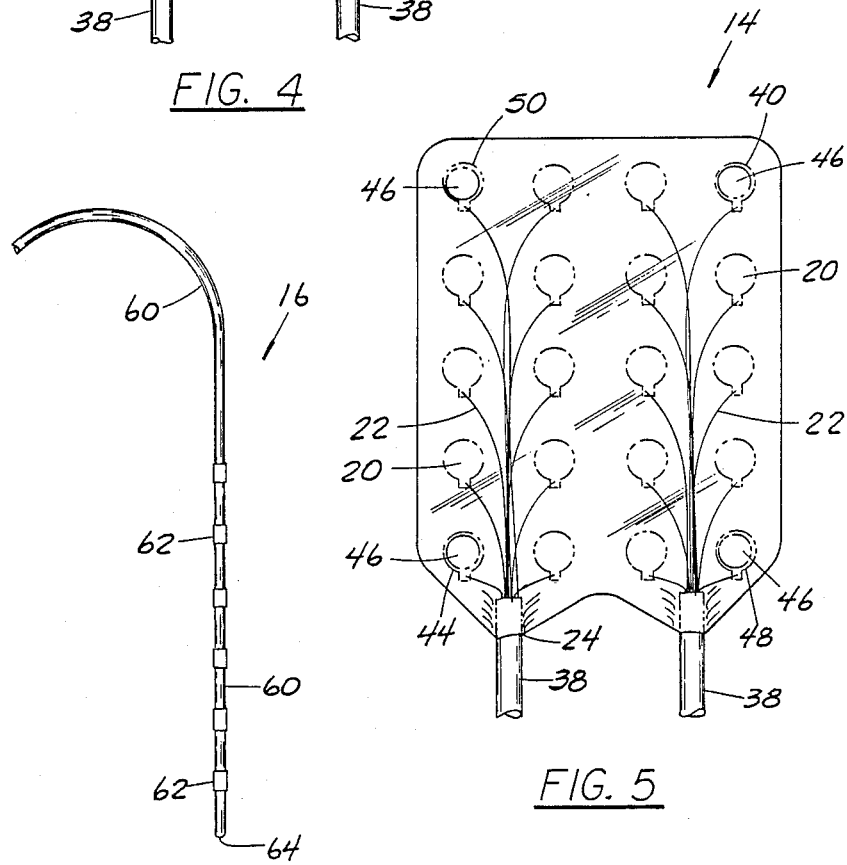
FIG. 6
FIG. 5

BRAIN-CONTACT FOR SENSING EPILEPTOGENIC FOCI WITH IMPROVED ACCURACY

FIELD OF THE INVENTION

This invention is related generally to sensing devices for use in defining epileptogenic foci and, more particularly, to electrical brain-contact devices for intracranial use in sensing procedures.

BACKGROUND OF THE INVENTION

Surgical removal of epileptogenic brain is indicated for treatment of many medically refractory focal seizure disorders. One of the important factors in providing good results from such surgery is the degree of accuracy in identifying epileptogenic foci. Various methods have been used in attempting to determine epileptogenic foci, and all, of course, involve sensing of cortical electrical activity using electrical contacts of various kinds applied in various ways.

In recent years many epilepsy centers have used intracranial recording techniques to better define regions of cortical epileptogenicity. Intracranial sensing techniques have used, broadly speaking, two different kinds of electrode members for engagement with brain tissue. Such different kinds of brain-contact devices include depth electrodes and flexible flat members which are known either as strip or grid electrodes, depending primarily on whether they have one or more rows of contacts.

These kinds of intracranial brain-contact devices each have a dielectric (non-conductive) base member on which an array of electrical contacts are mounted in spaced fashion. Separate leads extend from each of the contacts through the dielectric base member and therefrom to connectors and monitoring equipment which form no part of this invention.

Depth electrodes typically have contact rings sleeved over and spaced along a dielectric tubular member, with the leads extending inside the tube in a direction away from the distal end of the depth electrode. An example of depth electrodes is shown in U.S. Pat. No. 4,245,645 (Arseneault et al.).

Subdural strip and grid electrodes each have an array of contacts mounted on a sheet-like flat dielectric base member. Such contacts and the leads therefrom are usually held between two thin layers of dielectric material which are joined as one in the assembly process. An example of subdural electrodes is shown in U.S. Pat. No. 4,735,208 (Wyler et al.).

Depth electrodes penetrate deep into the brain tissue in direct contact with such tissue, while strip or grid electrodes are placed subdurally in direct contact with brain tissue at the surface of the brain, without penetrating brain tissue.

For each type of tissue-engagement member used in the prior art for monitoring electrical activity in the brain, the procedures for placement and hookup are of great importance. Accuracy of placement puts the contacts in the most advantageous positions for the period of observations which follows.

Observation periods often extend for days, one to three weeks being common. During such period the positions of the brain-contact devices can change to some extent. Furthermore, in some cases physicians may be somewhat uncertain for various reasons about precise locations of brain-contact devices even immediately after insertion.

Changes in electrode position are particularly likely for subdural strip and grid electrodes. Such subdural electrodes, unlike depth electrodes which are lodged in tissue, are somewhat free to move in their position between the dura and the brain tissue. Patient activities during an extended observation period can make such changes in position more likely.

Knowing the precise locations of the contacts of such electrical brain-contact devices is essential for accurate interpretation of the electrical readings which they sense. Electrical discharges picked up by intracranial contacts can be accurately associated with a specific location in the brain only to the extent that the precise locations of the contacts vis-a-vis the brain are known. Accurate knowledge about contact positions is essential for accurate determination of epileptogenic foci.

Since surgical removal of diseased brain cells is an intended subsequent course of action, accuracy in determining the location of diseased cells is of paramount importance. The substantial risks involved with removal of brain tissue are apparent. Accurate knowledge about the intracranial locations of the electrical contacts is critically important to successful subsequent surgical removal of diseased brain cells with minimum risk.

It is, therefore, desirable to make post-insertion checks on the precise location of the array of contacts of intracranial brain-contact devices, using x-rays. However, such location checks have been difficult at best primarily because of the nature of the electrical contacts. This is particularly the case with subdural strip and grid electrodes, in which the metal contacts, particularly the disks of subdural strip and grid electrodes, are themselves so thin and delicate that they cannot be seen or seen readily at desired x-ray powers.

There is a significant need for an improved electrical brain-contact device allowing a high degree of post-insertion confidence with respect to the intracranial positions of the electrical contacts.

OBJECTS OF THE INVENTION

It is an object of this invention to provide an improved electrical brain-contact device overcoming the problems and shortcomings of the prior art mentioned above.

Another object of this invention is to provide an improved electrical brain-contact device improving accuracy in determination of epileptogenic foci.

Another object of this invention is to provide an improved electrical brain-contact device the post-insertion intracranial positions of which can readily be determined.

Another object of this invention is to provide an improved electrical brain-contact device the intracranial position of which can readily be determined by x-ray at acceptable x-ray power.

These and other important objects will be apparent from the descriptions of this invention which follow.

SUMMARY OF THE INVENTION

This invention is an improvement in intracranial electrical brain-contact devices of the type having a dielectric base member, an array of contacts mounted on the dielectric base in spaced fashion, and separate leads extending from each contact. The brain-contact devices of this invention have radiopaque dielectric means adjacent to at least one of the electrical contacts such that the intracranial positions of the contacts of the array may readily be determined by x-ray at acceptable x-ray power.

Certain preferred embodiments also have a radiopaque dielectric sheathing extending from the base and enclosing the leads. Such radiopaque sheathing, combined with the aforementioned radiopaque dielectric means adjacent to at least one electrode, provides enhanced clarity facilitating observation of the location of the electrical contacts.

In certain preferred embodiments, the radiopaque dielectric means adjacent to at least one of the contacts is at least one discrete radiopaque dielectric marker. In other preferred embodiments, there are a plurality of radiopaque dielectric markers. In certain of the latter cases the radiopaque dielectric markers form a subarray corresponding in number and positions to a subset of the contacts. As in other embodiments, this indicates the positions of all contacts. The position of all contacts is known because the dielectric base members are made such that, despite their flexibility (as is particularly the case for subdural strip and grid electrodes), they maintain particular predetermined shapes.

In the preferred subdural strip and grid electrodes of this invention, as with other subdural strip and grid electrodes, the dielectric base member is a substantially flat flexible member and the contacts are substantially flat members within and substantially coplanar with the flexible member. The contacts have an exposed side and a covered side. The leads from such contacts are also within such flexible dielectric base member. And the radiopaque dielectric means is also held within the flexible member.

In such embodiments, the dielectric base member, as is the case in subdural strip and grid electrodes of the prior art, is preferably formed of first and second layers. The contacts are sandwiched between the first and second layers with the first layer having openings aligned with the contacts.

In such embodiments, the radiopaque dielectric marker or markers are preferably discrete substantially flat radiopaque dielectric pieces held between the first and second layers. In highly preferred embodiments, such radiopaque dielectric pieces are between the second layer and the electrical contacts which they mark.

One or more radiopaque dielectric sheathings, as mentioned above, preferably extend from the proximal edge of the dielectric base member in such embodiments.

In certain preferred embodiments of this invention, the radiopaque dielectric means is the dielectric base member itself. In such cases, determination of contact positions over such base member are facilitated despite delicacy and lack of significant x-ray opacity of such contacts at desirable x-ray settings. This is believed to be because, while the x-ray opacity of the contacts is normally insufficient, the incremental opacity provided by such contacts can be seen against the enhanced opacity of the radiopaque dielectric base member.

This embodiment, in one form, is a depth electrode in which the dielectric tubing forming the base member for the contact sleeves is itself radiopaque. While the contacts are delicate metallic sleeves, they can be observed at acceptable x-ray settings against the radio opacity of the radiopaque dielectric tubing forming the base member.

The radiopaque dielectric members are preferably dielectric plastic material filled with barium sulfate in their formation. However, as noted hereafter, a variety of other radiopaque fillers can be used.

BRIEF DESCRIPTION OF THE DRAWINGS

FIG. 4 is an enlarged bottom plan view of a grid electrode which is another electrical brain-contact device in accordance with this invention.

FIG. 5 is a similar bottom plan view of a variation of the embodiment of FIG. 4.

FIG. 6 is an elevation of a depth electrode which is still another preferred electrical brain-contact device in accordance with this invention.

DETAILED DESCRIPTIONS OF PREFERRED EMBODIMENTS

Figure 1:
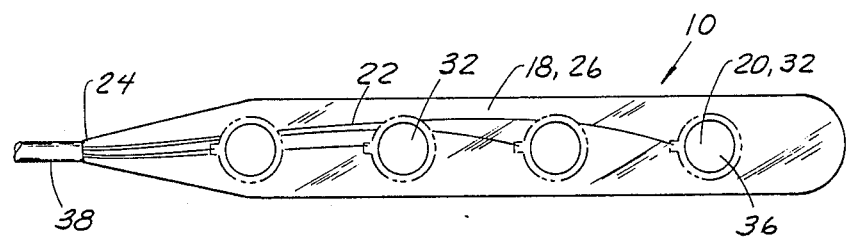
FIG. 1 is an enlarged plan view of a subdural strip electrode which is a preferred electrical brain-contact device in accordance with this invention.
Figure 2:
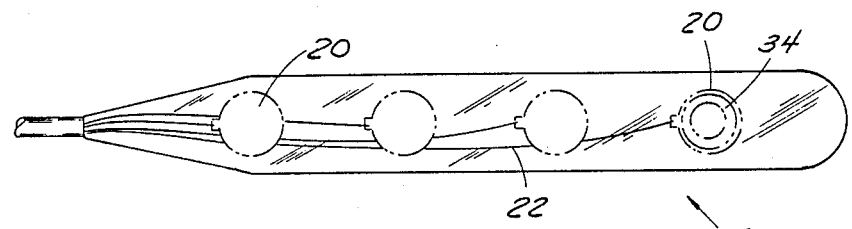
FIG. 2 is a bottom view of FIG. 1.
Figure 3:
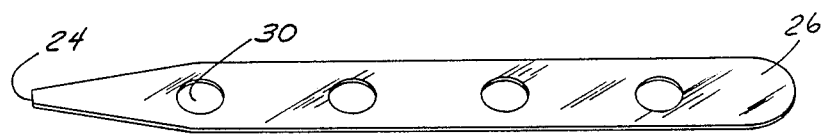
FIG. 3 is an exploded perspective view of FIG. 1.

The figures illustrate several preferred embodiments of this invention. The electrical brain-contact device of FIGS. 1–3 is a subdural strip electrode 10. The electrical brain-contact devices of FIGS. 4 and 5 are grid electrodes 12 and 14. The electrical brain-contact device of FIG. 6 is a depth electrode 16. Similar numbers will be used for parts which are identical in the embodiments illustrated.

Subdural strip electrode 10 is of the type having an elongated flexible silicone dielectric strip or base member 18, a row of several space aligned flat electrical stainless steel contact disks ("contacts") 20 which are held within flexible strip 18, and separate leads 22 attached to each of the contacts 20 and extending therefrom through the flexible dielectric strip 18 to a proximal edge 24 thereof where they exit strip 18.

Flexible dielectric strip or base member 18 has first and second (or top and bottom) dielectric layers 26 and 28. First layer 26 has openings 30, one for each contact 20. Openings 30 are circular and somewhat smaller in diameter than contacts 20. Each opening 30 serves to expose the face 32 of a contact 20 to allow contact with brain tissue. First and second dielectric layers 26 and 28 are sealed together by adhesive and/or heat such that they form, in essence, integral flexible strip 18.

In addition to supporting contacts 20, flexible dielectric strip 18 supports a flat radiopaque dielectric ring (marker) 34 in position between distal contact 36 and second dielectric layer 28. Dielectric ring 34 is sandwiched between distal contact 36 and second layer 28, being held in place between first and second dielectric layers 26 and 28 by virtue of their sealed, essentially integral relationship. Flexible dielectric strip or base member 18 also supports and encloses leads 22.

Flexible dielectric strip 18 is of a material which allows it to conform closely to the shapes of leads 22, contacts 20 and radiopaque dielectric marker ring 34. This allows flexible strip 18 to hold such elements securely in place.

A preferred material for dielectric layers 26 and 28, which form flexible strip 18, is silicone. A preferred silicone material is the silicone sheeting sold under the trademark SILASTIC by Dow Chemical Company, Midland, Michigan. The preferred adhesive used between first and second layers 26 and 28 is a type A Dow adhesive.

Leads 22, as they pass other contacts along the strip, extend along second dielectric layer 28 beneath the contacts. Leads 22 are electrically secured to their respective contacts 20 by soldering or otherwise. In the illustrated embodiment, there are four contacts 20. Thus, four leads 22 come together at proximal edge 24 of flexible strip 18.

Each lead 22 is a very fine stainless steel strand which is coated with TEFLON tetrafluoroethylene such that electrical contact is not made with the other contacts 20 which it passes as it extends to proximal edge 24. The diameter of leads 22, including their TEFLON insulation, is preferably on the order of 0.38 mm. (TEFLON is a trademark of DuPont Company, Wilmington, Delaware.)

Secured to proximal edge 24 of flexible dielectric strip 18 is a radiopaque dielectric sheathing 38. All leads 22 are enclosed within radiopaque sheathing 38 which extends from flexible dielectric strip 18 toward connectors and the equipment which is used for recording electrical impulses received by each contact 20.

The assembly procedure may be generally as follows: Layers 26 and 28 are cut properly and leads 22 are electrically secured to their respective contacts 20. Adhesive is applied to second dielectric layer 28, and contacts 20 are placed on second dielectric layer 28 at the appropriate locations, beginning with the contact closest to proximal edge 24. In each case the corresponding lead is laid across strip 10 to exit at proximal edge 24.

Prior to placement of distal contact 36, radiopaque dielectric ring 34 is placed on second layer 28; then distal contact 36 is laid over ring 34. After all the elements are laid on second layer 28, first layer 26 is placed thereover to sandwich such elements in place. Heat is applied such that the two silicone layers form flexible dielectric strip as an integral dielectric web.

Assembly methods form no part of this invention. Various other assembly methods could be used. Acceptable methods would be apparent to those skilled in the art who are made aware of this invention.

While the thinness of contacts 20 make them difficult to locate by x-ray, the inclusion of radiopaque dielectric marker ring 34 against distal contact 36 and radiopaque dielectric sheathing 38 extending from proximal edge 24 allow, or greatly facilitate, determination of intracranial positions of contacts 20 by x-ray at desirable x-ray settings. Subdural strip electrode 10, during its use, is located between the dura and the gray matter. X-ray viewing of the positions of radiopaque dielectric ring 34 and radiopaque sheathing 38 provides precise knowledge of the positions of each of contacts 20 along strip 10.

Radiopaque dielectric sheathing 38 is preferably a silicone material filled with barium sulfate. One particularly acceptable tubing of this type has about 13% by weight barium sulfate. It is sold by Dow Chemical Company under the trademark SILASTIC.

Radiopaque dielectric ring 34 is a thin substantially flat ring of the same radiopaque material. The ring may be a narrow cut segment of such radiopaque silastic tubing. An alternative material is a polyurethane similarly filled with barium sulfate. Such polyurethane tubing is available from Thermedics, Inc., Woburn, Massachusetts, under the trademark TECOFLEX.

Other materials may be used instead of barium sulfate as a filler to enhance radiopacity. Among such materials are bismuth subcarbonate and bismuth trioxide. Other suitable materials may be used to enhance radiopacity of such dielectric materials.

While subdural strip electrode 10 has a single row of contacts 20, grid electrodes 12 and 14 of FIGS. 4 and 5 have arrays of contacts 20 which include four rows with five contacts each. The construction of grid electrodes 12 and 14 is similar to that of strip electrode 10. That is, each has a similar flexible dielectric strip or base 18 which is formed from two layers, and the contacts and leads are similar to those of strip electrode 10. Extending from proximal edge 24 of the flexible dielectric material 18 of grid electrodes 12 and 14 are two dielectric sheathings 38. Such sheathings are radiopaque dielectric sheathings as previously described.

Grid electrode 12, as shown in FIG. 4, has three radiopaque dielectric ring markers 34 arranged in a particular way to aid in determination of the position of each of the contacts 20 of such device. In FIG. 4, radiopaque dielectric rings 34 are located adjacent to a first contact 40 which is at the upper right hand corner as seen in FIG. 4, a second contact 42 which is immediately adjacent to first contact 40, and a last contact 44 which is at a position diagonally opposite the position of first contact 40.

Thus, radiopaque dielectric rings 34 in FIG. 4 form a sub-array of markers which correspond in number and positions to a subset of contacts 20. Even without the use of radiopaque dielectric sheathings which orient grid electrode 12 in x-ray observation, the sub-array of markers facilitates x-ray determination of the orientation of the grid electrode and thus determines the position of each contact of the device of FIG. 4.

Grid electrode 14 of FIG. 5 differs from grid electrode 12 of FIG. 4 in several respects. First, it has four radiopaque markers rather than three. Second, such radiopaque markers are disks 46, rather than rings. And third, the marker placement is somewhat different. Radiopaque dielectric disks 46 are located adjacent to first contact 40 and last contact 44, each positioned as in the device of FIG. 4, and adjacent to contacts 48 and 50, which are in the lower right-hand and upper left-hand corners, as shown in FIG. 5.

Radiopaque dielectric disks 46 may be cut from radiopaque dielectric sheeting or sliced from a solid rod-shaped piece of radiopaque dielectric material.

While using a sub-array of radiopaque dielectric markers which correspond to a subset of contacts is acceptable and even desirable, it is possible to place a radiopaque dielectric marker adjacent to every contact of the contact array. And, the markers can be different to distinguish one contact from another.

The radiopaque dielectric markers can be in the form of separate pieces added to the flat constructions as shown, or they can be incorporated within the flexible member in other ways. For example, the flexible dielectric sheets can have radiopaque enhanced portions incorporated therein during their formation processes.

FIG. 6 shows depth electrode 16 which illustrates still another embodiment of this invention. Depth electrode 16 has a radiopaque tubing 60 as its dielectric base member. Spaced along radiopaque dielectric tubing 60 are delicate metallic sleeves 62 which serve as contacts. Leads extend from each of sleeve 62 within and along radiopaque dielectric tubing 60 in a direction away from distal end 64 thereof, that is, in a direction toward connectors and monitoring equipment. The construction of depth electrode 16 is generally similar to that of depth electrodes of the prior art.

The radiopaque dielectric tubing 60 allows depth electrode 16 to be readily observed by x-ray. Furthermore, such radiopaque dielectric tubing allows ready observation and determination by x-ray of the positions of contact sleeves 62, despite their delicacy and lack of significant x-ray opacity.

Radiopaque dielectric tubing 60 is preferably made of a dielectric silicone material filled with barium sulfate or a polyurethane material filled with barium sulfate. Acceptable silicone materials, as noted, are sold under the trademark SILASTIC by Dow Chemical Company. Acceptable polyurethane materials are sold under the trademark TECOFLEX by Thermedics, Inc.

The improved electrical brain-contact devices of this invention, and numerous variations thereof, may be made using well known materials and construction techniques. Acceptable materials and techniques would be apparent to those skilled in the art who are familiar with this invention. In addition to the preferred stainless steel used for contacts and leads, materials such as platinum or silver may be used.

While the principles of this invention have been described in connection with specific embodiments, it should be understood clearly that these descriptions are made only by way of example and are not intended to limit the scope of the invention.

What is claimed is:

1. In an electrical brain-contact device for sensing and mapping electrical epileptogenic discharges within the brain of the type having a dielectric base member and an array of electrical sensing contacts mounted thereon in spaced fashion with separate leads extending therefrom, the improvement comprising a radiopaque dielectric material adjacent to at least one of the sensing contacts whereby the intracranial positions of the sensing contacts of the array may readily be determined by x-ray without effect on the electrical sensing qualities of the sensing contacts.

2. The electrical brain-contact device of claim 1 further including a radiopaque, dielectric sheathing extending from the base member and enclosing the leads.

3. The electrical brain-contact device of claim 1 wherein the radiopaque dielectric material comprises at least one discrete radiopaque dielectric marker.

4. The electrical brain-contact device of claim 3 wherein said discrete radiopaque dielectric marker is substantially flat.

5. The electrical brain-contact device of claim 3 further including a radiopaque dielectric sheathing extending from the base member and enclosing the leads.

6. The electrical brain-contact device of claim 3 comprising a plurality of said radiopaque dielectric markers.

7. The electrical brain-contact device of claim 6 wherein said radiopaque dielectric markers form a subarray corresponding in number and positions to a subset of the contacts, thereby indicating positions of all contacts.

8. The electrical brain-contact device of claim 1 wherein the radiopaque dielectric material is said base member itself, thereby facilitating determination of contact positions despite delicacy and lack of significant x-ray opacity of such contacts at desirable x-ray settings.

9. The electrical brain-contact device of claim 1 wherein:
the dielectric base member is a substantially flat flexible member;
the contacts are substantially flat members within and substantially coplanar with the flexible member, the contacts having an exposed side and a covered side; and
the radiopaque dielectric material is held within the flexible member.

10. The electrical brain-contact device of claim 9 wherein the flexible member includes a proximal edge and at least one radiopaque dielectric sheathing extends from the base member and encloses a plurality of the leads.

11. The electrical brain-contact device of claim 9 wherein the array is a single row of contacts, the radiopaque dielectric material including a marker for at least one contact.

12. The electrical brain-contact device of claim 11 wherein the flexible member includes a proximal edge and a radiopaque dielectric sheathing extends from the base member enclosing the leads.

13. The electrical brain-contact device of claim 9 wherein the dielectric radiopaque material is a plurality of discrete radiopaque dielectric markers.

14. The electrical brain-contact device of claim 13 wherein the radiopaque dielectric markers form a subarray corresponding in number and positions to a subset of the contacts, thereby indicating positions of all contacts.

15. The electrical brain-contact device of claim 14 wherein the contact array has a plurality of rows of said contacts.

16. The electrical brain-contact device of claim 1 wherein:
the dielectric base member is a substantially flat flexible member having first and second layers;
the contacts are substantially flat members sandwiched between the first and second layers, the first layer having openings aligned with the contacts; and
the radiopaque dielectric material is at least one discrete substantially flat radiopaque dielectric marking piece held between the first and second layers.

17. The electrical brain-contact device of claim 1 wherein:
the dielectric base member is a radiopaque tube; and
the contacts are delicate metallic sleeves on the radiopaque tube,
thereby forming a depth-electrode device with contacts the positions of which can readily be determined by x-ray despite their delicacy and lack of significant x-ray opacity at desirable x-ray settings.

18. In an electrical brain-contact device of the type having a substantially flat flexible dielectric base member with first and second layers and an array of substantially flat contacts sandwiched between the first and second layers in spaced fashion with separate leads extending therefrom, the first layer having openings aligned with the contacts, the improvement comprising at least one discrete substantially flat radiopaque dielectric marking piece held between the second layer and at least one of the contacts, whereby the intracranial positions of the contacts of the array may readily be determined by x-ray.

19. The electrical brain-contact device of claim 18 having a plurality of said flat radiopaque dielectric marking pieces.

20. The electrical brain-contact device of claim 19 wherein the radiopaque dielectric marking pieces form a sub-array corresponding in number and positions to a subset of the contacts, thereby indicating positions of all contacts.

* * * * *

UNITED STATES PATENT AND TRADEMARK OFFICE
CERTIFICATE OF CORRECTION

PATENT NO. : 4,903,702

DATED : February 27, 1990

INVENTOR(S) : David A. Putz

It is certified that error appears in the above-identified patent and that said Letters Patent is hereby corrected as shown below:

In column 4, line 31, change "space" to --spaced--.

In claim 1, line 6, after "comprising" remove the word "a".

In claim 2, line 2, after "radiopaque" remove the ",".

Signed and Sealed this

Twenty-sixth Day of February, 1991

Attest:

HARRY F. MANBECK, JR.

*Attesting Officer*  *Commissioner of Patents and Trademarks*